United States Patent
Ashley et al.

(10) Patent No.: US 11,428,691 B2
(45) Date of Patent: Aug. 30, 2022

(54) METHODS FOR PREDICTING TUMOR RESPONSE TO IMMUNOTHERAPY

(71) Applicant: Duke University, Durham, NC (US)

(72) Inventors: David Ashley, Durham, NC (US); Darell Bigner, Mebane, NC (US); Matthias Gromeier, Durham, NC (US); Smita Nair, Durham, NC (US)

(73) Assignee: Duke University, Durham, NC (US)

( * ) Notice: Subject to any disclaimer, the term of this patent is extended or adjusted under 35 U.S.C. 154(b) by 111 days.

(21) Appl. No.: 16/961,018

(22) PCT Filed: Jan. 23, 2019

(86) PCT No.: PCT/US2019/014761
§ 371 (c)(1),
(2) Date: Jul. 9, 2020

(87) PCT Pub. No.: WO2019/147681
PCT Pub. Date: Aug. 1, 2019

(65) Prior Publication Data
US 2021/0063398 A1    Mar. 4, 2021

Related U.S. Application Data

(60) Provisional application No. 62/787,508, filed on Jan. 2, 2019, provisional application No. 62/620,577, filed on Jan. 23, 2018.

(51) Int. Cl.
| | | |
|---|---|---|
| *G01N 33/574* | (2006.01) | |
| *A61P 35/00* | (2006.01) | |
| *A61K 39/13* | (2006.01) | |
| *C12Q 1/6886* | (2018.01) | |
| *A61K 45/06* | (2006.01) | |
| *A61K 39/00* | (2006.01) | |

(52) U.S. Cl.
CPC ........... *G01N 33/574* (2013.01); *A61K 39/13* (2013.01); *A61P 35/00* (2018.01); *C12Q 1/6886* (2013.01); *A61K 45/06* (2013.01); *A61K 2039/585* (2013.01); *G01N 2800/52* (2013.01)

(58) Field of Classification Search
CPC .................................................. G01N 33/574

USPC ........................................................ 435/7.23
See application file for complete search history.

(56) References Cited

FOREIGN PATENT DOCUMENTS

WO    2019147681 A1    8/2019

OTHER PUBLICATIONS

Holl et al (Oncotarget, 2016, 7(48): 79828-79841) teaches PVSRIPO (Abstract, in particular).*
Snyder et al (NEJM, 2014, 371: 2189-2199).*
Yarchoan et al. Tumor Mutational Burden and Response Rate to PD-1 Inhibition The New England Journal of Medicine, vol. 377, No. 25, Dec. 21, 2017, pp. 2500-2501.
Database Embase [Online], Elsevier Science Publishers, Amsterdam, NL; Nov. 1, 2017, Walton et al. "PVSRIPO is an interferon-resistant, immunotherapeutic oncolytic virus" Databse accession No. EMB-619371339 *abstract* & Journal for Immunotherapy of Cancer 20171101 Biomed Central Ltd. Nld, vol. 5, No. Supplement 2.
Oct. 4, 2021—(EP) Extended European Search Report—Appln No. 19744395.5.
Spigel, et al. Rationale for Chemotherapy, Immunotherapy, and Checkpoint Blockade in SCLC: Beyond Traditional Treatment Approaches. J Thorac Oncol. 2013, 8(5):587-98; Abstract, p. 588, col. 1.
Yarchoan, et al. Tumor Mutational Burden and Response Rate to PD-1 Inhibition. N Engl J Med. 2017, 377(25): 2500-2501.
Jul. 5, 2019—International Search Report ISA_210—Application No. PCT/US2019/014761.
Jul. 5, 2019—Written Opinion ISA_237—Application No. PCT/US2019/014761.

* cited by examiner

*Primary Examiner* — Sean E Aeder
(74) *Attorney, Agent, or Firm* — Banner & Witcoff, Ltd.

(57) ABSTRACT

Methods of testing tumor samples for mutational burden and/or for expression profiles permit the prediction of responsiveness of an individual to immunotherapy comprising PVSRIPO. Those predicted to respond are treated with PVSRIPO and those predicted not to respond are treated with other agents.

15 Claims, 7 Drawing Sheets

Specification includes a Sequence Listing.

| Patient | Chr | Start | SBS | Gene.refGene | ExonicFunc.refGene | PROVEAN PREDICTION (cutoff=2.5) | SIFT PREDICTION (cutoff=0.05) |
|---|---|---|---|---|---|---|---|
| 14 | chr7 | 45614710 | G>A | ADCY1 | nonsynonymous SNV | Neutral | Tolerated |
| 14 | chr16 | 3900687 | C>T | CREBBP | nonsynonymous SNV | Neutral | Tolerated |
| 14 | chr8 | 11705250 | G>A | CTSB | nonsynonymous SNV | Deleterious | Damaging |
| 14 | chr19 | 40318020 | C>T | DYRK1B | nonsynonymous SNV | Neutral | Tolerated |
| 14 | chr6 | 24780913 | C>T | GMNN | nonsynonymous SNV | Deleterious | Damaging |
| 14 | chr15 | 67938771 | G>A | MAP2K5 | nonsynonymous SNV | Deleterious | Damaging |
| 14 | chr1 | 153660245 | G>A | NPR1 | nonsynonymous SNV | Neutral | Tolerated |
| 14 | chr17 | 5049354 | G>A | USP6 | nonsynonymous SNV | Deleterious | Damaging |
| 14 | chr3 | 44959440 | C>T | ZDHHC3 | nonsynonymous SNV | Neutral | Tolerated |
| 18 | chr10 | 96731943 | C>T | CYP2C9 | nonsynonymous SNV | Deleterious | Damaging |
| 28 | chr14 | 24801065 | G>A | ADCY4 | nonsynonymous SNV | Deleterious | Tolerated |
| 28 | chr2 | 202712183 | G>A | CDK15 | nonsynonymous SNV | Neutral | Tolerated |
| 28 | chr16 | 3900600 | G>A | CREBBP | nonsynonymous SNV | Neutral | Tolerated |
| 28 | chr8 | 11703230 | C>T | CTSB | nonsynonymous SNV | Deleterious | Damaging |
| 28 | chr10 | 96745844 | C>T | CYP2C9 | nonsynonymous SNV | Deleterious | Tolerated |
| 28 | chr3 | 42916147 | G>A | CYP8B1 | nonsynonymous SNV | Deleterious | Damaging |
| 28 | chr19 | 40316464 | G>A | DYRK1B | nonsynonymous SNV | Neutral | Damaging |
| 28 | chr14 | 34396221 | C>T | EGLN3 | stopgain | NA | NA |
| 28 | chr11 | 120690539 | C>T | GRIK4 | nonsynonymous SNV | Deleterious | Damaging |
| 28 | chr11 | 120776023 | G>A | GRIK4 | nonsynonymous SNV | Neutral | Tolerated |
| 28 | chr7 | 97736572 | C>T | LMTK2 | nonsynonymous SNV | Deleterious | Damaging |
| 28 | chr7 | 97823274 | C>T | LMTK2 | nonsynonymous SNV | Deleterious | Damaging |

FIG. 6

| | | | | | | | |
|---|---|---|---|---|---|---|---|
| 28 | chr8 | 56864557 | C>T | LYN | nonsynonymous SNV | Neutral | Tolerated |
| 28 | chr15 | 67984826 | C>T | MAP2K5 | nonsynonymous SNV | Deleterious | Damaging |
| 28 | chr15 | 67995703 | G>A | MAP2K5 | nonsynonymous SNV | Neutral | Damaging |
| 28 | chrX | 100118509 | G>A | NOX1 | nonsynonymous SNV | Deleterious | Damaging |
| 28 | chr1 | 153661464 | C>T | NPR1 | nonsynonymous SNV | Deleterious | Damaging |
| 28 | chr1 | 153665582 | C>T | NPR1 | nonsynonymous SNV | Deleterious | Damaging |
| 28 | chr6 | 27879389 | C>T | OR2B2 | nonsynonymous SNV | Deleterious | Damaging |
| 28 | chr8 | 42227461 | G>A | POLB | nonsynonymous SNV | Deleterious | Damaging |
| 28 | chr14 | 78221456 | G>A | SNW1 | nonsynonymous SNV | Deleterious | Damaging |
| 28 | chr1 | 109940306 | G>A | SORT1 | nonsynonymous SNV | Neutral | Damaging |
| 28 | chr3 | 45000818 | C>T | ZDHHC3 | stopgain | NA | NA |
| 28 | chr14 | 24793267 | C>T | ADCY4 | splicing | NA | NA |
| 28 | chr19 | 10906116 | G>A | DNM2 | splicing | NA | NA |
| 28 | chr15 | 69318992 | G>A | NOX5 | splicing | NA | NA |
| 28 | chr1 | 182573350 | C>T | RGS16 | splicing | NA | NA |
| 48 | chr7 | 97800925 | A>G | LMTK2 | nonsynonymous SNV | Deleterious | Damaging |
| 64 | chr1 | 153655001 | G>T | NPR1 | nonsynonymous SNV | Deleterious | Tolerated |
| 11A | chr14 | 78184661 | T>G | SNW1 | nonsynonymous SNV | Neutral | Tolerated |
| 20A | chr17 | 5037278 | C>T | USP6 | stopgain | NA | NA |

FIG. 6
CONTINUED

SEQUENCE LISTING

```
<160> NUMBER OF SEQ ID NOS: 1

<210> SEQ ID NO 1
<211> LENGTH: 15
<212> TYPE: RNA
<213> ORGANISM: Poliovirus

<400> SEQUENCE: 1
aaaaaaaaaa aaaaa                                               15
```

METHODS FOR PREDICTING TUMOR RESPONSE TO IMMUNOTHERAPY

TECHNICAL FIELD OF THE INVENTION

This disclosure relates to cancer diagnostics and companion diagnostics for cancer immunotherapies. More particularly, the invention relates to detection of one or more mutations, or a profile comprising a group of mutations, that are useful for diagnosis, prognosis, and for predicting the therapeutic effectiveness of treatment of cancer including by immunotherapeutic agents. Certain gene expression profiles may be used as surrogates for detection of mutations.

BACKGROUND OF THE INVENTION

PVSRIPO is an oncolytic poliovirus (PV) recombinant. It consists of the live attenuated type 1 (Sabin) PV vaccine containing a foreign internal ribosomal entry site (IRES) of human rhinovirus type 2 (HRV2). The IRES is a cis-acting genetic element located in the 5' untranslated region of the PV genome. The virus has shown exciting signs of efficacy in humans when used as an immunotherapeutic agent to treat cancer. However, individuals receiving PVSRIPO treatment for cancer can respond with different clinical outcomes. Definition of a genetic or biochemical basis for recognizing which individuals will derive the most benefit from treatment with immunotherapeutic agents remains a significant unmet medical need. Such a basis would help medical professionals plan for alternative therapies or treatment modalities for those individuals who are not likely to respond to immunotherapeutic agents.

SUMMARY OF THE INVENTION

One aspect of the invention is a method of treating an individual having a tumor A tumor sample from the individual is tested and its tumor mutational burden is determined. Upon determining a high mutational burden in the tumor sample, a therapy that does not comprise PVSRIPO is administered to the individual. Upon determining a low mutational burden in the tumor sample, an immunotherapeutic agent comprising PVSRIPO is administered to the individual.

Another aspect of the invention is a method for predicting response of an individual with cancer to treatment with an immunotherapeutic agent comprising PVSRIPO. A tumor sample from the individual is tested and a high or a low tumor mutational burden is detected. When a high tumor mutational burden is detected in the tumor sample, one predicts that the individual is not likely to respond with a therapeutic effect to treatment with PVSRIPO. Alternatively, when a low tumor mutational burden is detected, one predicts that the individual is likely to respond with a therapeutic effect to treatment with PVSRIPO.

Still another aspect of the invention is a method of determining if a treatment regimen for an individual with cancer should include treatment with PVSRIPO. A tumor sample from the individual with cancer is tested and tumor mutational burden is detected. When a high tumor mutational burden is detected, one determines that the treatment regimen will not include PVSRIPO and the individual will not be treated with PVSRIPO.

Yet another aspect of the invention is a method of determining if a treatment regimen for an individual with cancer should include treatment with PVSRIPO. A tumor sample from the individual with cancer is tested and tumor mutational burden is detected. When a low tumor mutational burden is detected one determines that the treatment regimen will include and the individual will be treated with PVSRIPO.

One aspect of the invention is a method of treating an individual having a tumor. A tumor sample from the individual is tested and expression of cytolytic activity genes, T-Cell Receptor (TCR) signaling genes, or inflammatory response genes is determined. Upon determining a low level of expression of cytolytic activity genes, T-Cell Receptor (TCR) signaling genes, or inflammatory response genes in the tumor sample, a therapy that does not comprise PVSRIPO is administered to the individual. Upon determining a high level of expression of cytolytic activity genes, T-Cell Receptor (TCR) signaling genes, or inflammatory response genes in the tumor sample, administering to the individual an immunotherapeutic agent comprising PVSRIPO.

A further aspect of the invention is a method for predicting response of an individual with cancer to treatment with an immunotherapeutic agent comprising PVSRIPO. A tumor sample from the individual is tested and a high or a low level of expression of cytolytic activity genes, T-Cell Receptor (TCR) signaling genes, or inflammatory response genes is determined. When a low level of expression of cytolytic activity genes, T-Cell Receptor (TCR) signaling genes, or inflammatory response genes is determined in the tumor sample, one predicts that the individual is not likely to respond with a therapeutic effect to treatment with PVSRIPO. When a high level of expression of cytolytic activity genes, T-Cell Receptor (TCR) signaling genes, or inflammatory response genes is determined, one predicts that the individual is likely to respond with a therapeutic effect to treatment with PVSRIPO.

Another aspect of the invention is a method of determining if a treatment regimen for an individual with cancer should include treatment with PVSRIPO. A tumor sample from the individual with cancer is tested and expression of cytolytic activity genes, T-Cell Receptor (TCR) signaling genes, or inflammatory response genes is determined. When a low level of expression of cytolytic activity genes, T-Cell Receptor (TCR) signaling genes, or inflammatory response genes is detected, one determines that the treatment regimen will not include PVSRIPO, and the individual will not be treated with PVSRIPO.

Still another aspect of the invention is a method of determining if a treatment regimen for an individual with cancer should include treatment with PVSRIPO. A tumor sample from the individual with cancer is tested and expression levels of cytolytic activity genes, T-Cell Receptor (TCR) signaling genes, or inflammatory response genes is determined. When a high level of said expression is detected, one determines that the treatment regimen will include PVSRIPO and the individual will be treated with PVSRIPO.

Tumor mutational burden (TMB) is a quantitative representation of the total number of mutations per a coding area of a tumor genome. We provide a method of treating an individual having a tumor possibly harboring tumor cells with genetic mutations, comprising: (a) testing; a sample of tumor from the individual and determining the tumor mutational burden, wherein if (i) a high tumor mutational burden is detected, the method comprises not administering to the individual an immunotherapeutic agent consisting of PVSRIPO; or (ii) a low tumor mutational burden is detected, administering to the individual an immunotherapeutic agent comprising PVSRIPO. In some embodiments, wherein in the method detected is a low tumor mutational burden, administered to the individual is an immunotherapeutic agent comprising PVSRIPO and, optionally, the method may further comprise administering a chemotherapeutic agent or immunotherapeutic agent other than PVSRIPO. In certain aspects, the immunotherapeutic agent may comprise a combination of PVSRIPO and another immunotherapeutic agent other than PVSRIPO (e.g., an immune checkpoint inhibitor). In one embodiment, the tumor comprises a solid nonlymphoid tumor. In another embodiment, the solid nonlymphoid tumor comprises a brain tumor. In a further embodiment, the brain tumor comprises glioblastoma.

In another embodiment of the method, the tumor mutational burden may comprise the extent of hypermutation in the tumor cells. For example, treatment of tumors with an alkylating agent may result in production of hypermutations within the tumor cells. A "hypermutated phenotype associated with treatment by an alkylating agent" comprises a pattern of hypermutation where greater than or equal to 80% of the somatic mutations detected comprise G:C>A:T transitions at non-CpG sites. Thus, a high tumor mutational burden in tumors having been treated with an alkylating agent may comprise a hypermutated phenotype associated with treatment by an alkylating agent. Also provided is a method of treating an individual having a tumor possibly harboring cells with genetic mutations, the method comprising: testing a sample of tumor from the individual for presence or absence of a hypermutated phenotype associated with treatment by an alkylating agent. If such hypermutated phenotype is present, the method comprises not administering to the individual an immunotherapeutic agent comprising PVSRIPO; or if the individual is receiving an immunotherapeutic agent comprising PVSRIPO, administering one or more of a chemotherapeutic agent, and an immunotherapeutic agent other than PVSRIPO. If such hypermutated phenotype is absent, the method comprises treating the individual with an immunotherapeutic composition comprising PVSRIPO. In one embodiment, the treatment with PVSRIPO is prior to treatment with an alkylating agent known to cause somatic hypermutation. Optionally, the method may further comprise administering a chemotherapeutic agent or immunotherapeutic agent other than PVSRIPO. In one embodiment, the tumor comprises a solid nonlymphoid tumor. In another embodiment, the solid nonlymphoid tumor comprises a brain tumor. In a further embodiment, the brain tumor comprises glioblastoma.

In some embodiments, the sample from the individual includes RNA, and the one or more mutations are detected using nucleic acid amplification techniques or detection techniques such as DNA sequencing, reverse transcription PCR (RT-PCR) or Fluorescence In Situ Hybridization (FISH). In some embodiments, the sample includes DNA, and the one or more mutations are detected using a nucleic acid amplification technique. In some embodiments, mutations are detected using an oligonucleotide, complementary to the mutant sequence to be detected. For example, allele-specific PCR or PCR (polymerase chain reaction) with an allele-specific probe, may be used to detect a mutation.

Further, we provide methods for determining the likelihood of response of an individual with cancer to therapy with an immunotherapeutic agent comprising PVSRIPO comprising: testing a sample of tumor from the individual for presence or absence of one or more of (a) tumor mutational burden, and (b) hypermutated phenotype associated with treatment by an alkylating agent. If, from the testing of the tumor sample there is one or more of: (i) a low tumor mutational burden, and (ii) absence of a hypermutated phenotype associated with treatment by an alkylating agent; the method comprises reporting that the individual will likely respond to treatment with an immunotherapeutic composition comprising PVSRIPO. A medical practitioner may then decide to include PVSRIPO in a treatment regimen for the individual with cancer, and may then treat the individual with PVSRIPO. If from the testing of tumor from the individual there is one or more of: (a) a high tumor mutational burden; and (c) a hypermutated phenotype associated with treatment by an alkylating agent; the method comprises reporting that the individual likely will not respond to treatment with an immunotherapeutic composition comprising PVSRIPO, or is unlikely to continue responding to an immunotherapeutic composition comprising PVSRIPO if the individual has received treatment with an immunotherapeutic composition comprising PVSRIPO. With a likelihood of not responding to an immunotherapeutic composition comprising PVSRIPO, a medical practitioner and the individual may consider a treatment regimen comprising an agent or modality other than PVSRIPO. In one embodiment, the tumor comprises a solid nonlymphoid tumor. In another embodiment, the solid nonlymphoid tumor comprises a brain tumor. In a further embodiment, the brain tumor comprises glioblastoma.

Also provided herein are kits for detecting mutations in a sample of an individual having tumor. The kit comprises oligonucleotides for specific detection of a hypermutated phenotype associated with treatment by an alkylating agent (e.g., of the somatic mutations detected, greater than or equal to 80% of the mutations comprise G:C>A:T transitions at non-CpG sites). In some embodiments, the kit further comprises reagents for carrying out amplification and detection using the included oligonucleotides, e.g., buffers, nucleic acid polymerase, reverse transcriptase, cofactors, dNTPs, detectable label, etc.

Further included are methods for predicting prognosis in an individual with cancer. In some embodiments, the method comprises determining the number of mutations in a sample of tumor from the individual; and predicting a worse prognosis (e.g., tumor progression, reduced progression free survival time, reduced overall survival time, etc.) for the individual if mutational burden detected in the tumor sample is high, e.g., comprises greater than or equal to 1.5, 1.6, 1.7, 1.8, 1.9, or 2.0 total mutations per megabase in the case of glioblastoma multiforme. As described below, the cut-off for high tumor burden may vary from tumor type to tumor type. In some embodiments, a tumor sample is selected from the group consisting of a tissue sample from the individual including tumor tissue, or a body fluid that is expected to comprise nucleic acid molecules (e.g., RNA or DNA) of tumor origin. In some embodiments, the mutations may be expressed as tumor mutational burden, wherein a presence of a high mutational burden is predictive of a worse prognosis. In some embodiments, the mutations may be expressed as a percentage of somatic mutations that comprise G:C>A:T transitions at non-CpG sites, wherein the presence of a hypermutated phenotype associated with treatment by an alkylating agent is predictive of a worse prognosis. In some embodiments, mutations for at least 10, 20, 30, 40, 50, 60, 70, 80, 90, 100, 200, 250, 300, 500, 1000, or more genes are tested for presence or absence of mutations.

These, and other aspects which will be apparent to those of skill in the art from the specification, illustrate new therapeutic regimens for treating cancer, as well as companion diagnostics for such treatment.

BRIEF DESCRIPTION OF THE DRAWINGS

FIG. 6 shows a list of 82 mutational variants in 42 genes across samples from 7 individuals who did not show clinical benefit from immunotherapy comprising PVSRIPO administration, including a propensity of C>T/G>A transitions (C to T mutations, G to A mutations).

DETAILED DESCRIPTION OF THE INVENTION

Figure 1:
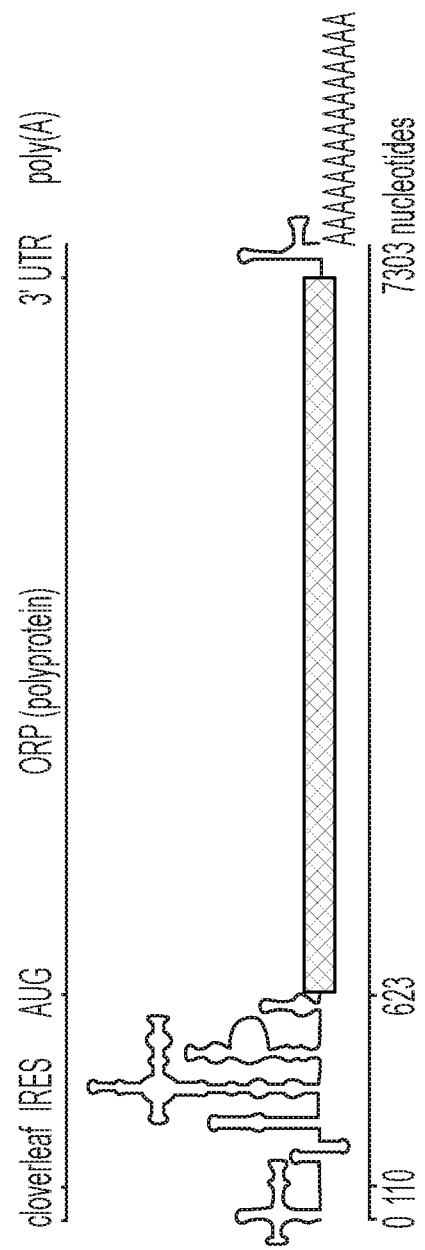
FIG. 1 is a schematic of a chimeric poliovirus comprising a Sabin type I strain of poliovirus with a human rhinovirus type 2 internal ribosome entry site ("IRES") in the 5" untranslated region of the poliovirus between its cloverleaf structure ("cloverleaf") and open reading frame ("ORF", solid black line).

Genomic alterations accumulated during tumorigenesis are increasingly recognized as playing a role in development of antitumor immune responses. In that regard, tumor mutational burden (TMB) has been used recently as a clinical marker or biomarker for predicting tumor responses to immunotherapy. Tumor mutational burden is a quantitative measure of the total number of mutations detected per area of tumor genome measured. Whole-exome sequencing of somatic mutations in samples of tumor from individuals has been used to predict response to immunotherapeutic agents in the class of immune checkpoint inhibitors. It has been demonstrated that immune checkpoint inhibitors, and particularly anti-CTLA4 antibodies and anti-PD1 antibodies, have shown a greater therapeutic effect in solid nonlymphoid tumors (e.g., melanoma, non-small cell lung carcinoma) with a high mutational burden (also termed "high mutational load") (Snyder et al., 2014, *N Engl J Med,* 371:2189-99; Liontos et al., 2016, *Ann Trend Med* 4(14): 264).

In contrast to the findings for immunotherapeutic agents such as checkpoint inhibitors where a high tumor mutational burden is associated with greater therapeutic effect, we show below that a low tumor mutational burden is associated with a greater therapeutic effect upon treatment of tumors by an immunotherapeutic agent known as PVSRIPO. While applicants do not wish to be hound by any mechanism or theory of action, the different effect of tumor mutational burden in these two treatment scenarios may relate to the mechanisms by which these therapeutic agents exert their effects. Checkpoint inhibitors are thought to work via the adaptive immune system, whereas PVSRIPO is believed to work via the innate immune system.

Alkylating chemotherapy agents are still used in first line therapy of various types of cancers. Many of the DNA lesions induced by alkylating chemotherapy agents are mutagenic and may contribute to a tumor mutational burden. For example, initial low-grade gliomas or recurrent tumors may have a low mutational load (e.g., 0.2 to 4.5 mutations per megabase of DNA), whereas a majority of tumors treated with temozolomide contain DNA that was hypermutated (e.g., contained 31.9 to 90.0 mutations per megabase) (Johnson et al. 2014, 343(6167):189-193). Somatic mutations in the mismatch repair genes, which encode mismatch repair proteins, usually increase after temozolomide treatment, resulting in resistance to treatment by temozolomide. Moreover, the hypermutation in the tumor genome is associated with a poor prognosis (Xie et al., 2016, *Mol. Clin. Oncol.* 5(2):236-240).

A hypermutated phenotype associated with treatment by an alkylating agent is when greater than or equal to 10 somatic variants per Mb of DNA occurs. Additionally, examination of the hypermutated DNA reveals that 80% of the mutations are single base pair mutations that are C>T/G>A transitions (also known as C:G>T:A transitions; C to T mutations, G to A mutations). In some samples from individuals who were treated with temozolomide, a vast majority of mutations detected (see FIG. 6) were C:G>T:A transitions. Thus, a hypermutated phenotype associated with treatment by an alkylating agent can yield both increased somatic variants in the tumor genome as well as a distinct mutational signature. Presence of such hypermutation is predictive of resistance to, or lack of a therapeutic effect of, treatment with an immunotherapeutic agent comprising PVSRIPO. Thus, a method of treating an individual having tumor possibly harboring cells with one or more genetic mutations, comprises: testing a tumor sample from the individual for the presence or absence of a hypermutated phenotype associated with treatment by an alkylating agent. If such hypermutated phenotype is present, the method further comprises not administering to the individual an immunotherapeutic agent comprising PVSRIPO, or if the individual is receiving an immunotherapeutic agent comprising PVSRIPO, administering a chemotherapeutic agent and/or an immunotherapeutic agent other than PVSRIPO. In an absence of a hypermutated phenotype associated with treatment by an alkylating agent, the method further comprises administering PVSRIPO to the individual, and, optionally, if the individual is to receive treatment with an alkylating agent, preferably PVSRIPO is administered prior to (first) or concurrent with administering an alkylating agent to the individual. Optionally, the method may further comprise administering a chemotherapeutic agent or immunotherapeutic agent other than PVSRIPO.

Tumor mutational burden varies among different tumor types. Some tumor types have a higher "natural" rate of mutation than others. These mutations occur during the course of tumorigenesis and are not induced by treatment with an alkylating agent. Even among these untreated tumors, there is a distribution of mutation rates. As described below, we have found that for glioblastomas, which have a relatively low mutation rate relative to other tumor types, that there is a distribution of mutation rates. Tumors that have less than 1.9 or less than 1.5 somatic variants per Mb are considered low TMB, while those with a rate that is greater than or equal to 1.9 or 1.5 somatic variants per Mb are considered high TMB. In some embodiments, the cutoff between high and low tumor mutational burden may be 1.5, 1.6, 1.7, 1.8, 1.9, or 2.0 for glioblastomas. As described for the high mutation rates caused by alkylating agents, the high TMB glioblastomas are refractory to effective therapy with PVSRIPO, whereas individuals with low TMB glioblastomas are much more likely to achieve a durable response to PVSRIPO. Determination of different groupings for high and low TMB for different tumors is discussed below in discussing tumor mutational burden.

Any technique for directly administering an immunotherapeutic agent comprising PVSRIPO to the tumor may be used. Direct administration does not rely on the blood vasculature to access the tumor. The preparation may be applied to a tumor microenvironment, injected into the tumor, introduced into or at the tumor site during surgery, infused into the tumor via a catheter, etc. One particular technique which may be used for introduction in to brain cancer is convection enhanced delivery. For methods involving administration of another therapeutic agent (such as one or more of a chemotherapeutic agent or immune checkpoint inhibitor) the therapeutic agent may be administered in a therapeutically effective amount and by any appropriate means known in the art for the particular therapeutic agent. These include intravenous, oral, intraperitoneal, sublingual, intrathecal, intracavitary, intramuscularly, and subcutaneously. Optionally, the therapeutic agent may be administered in combination with an immunotherapeutic agent comprising PVSRIPO. The therapeutic agent may be administered at the same time, before, or after an immunotherapeutic agent comprising PVSRIPO. Typically, the two agents will be administered within 30, 28, 21, 14, 7, 4, 2, or 1 day(s) of each other. The agents may be given repeatedly, either serially or in a cycle of first and second agents. It may be advantageous but not necessary for an immunotherapeutic agent comprising PVSRIPO to be administered prior to administration of a checkpoint inhibitor; but the reverse order may also be used. Induction of an antitumor immune response following administration of an immunotherapeutic agent comprising PVSRIPO may take from about 5 to about 14 days. Administration of the checkpoint inhibitor or chemotherapeutic agent may beneficially be commenced during or after the priming period.

Kits may be used for detecting mutations in a sample of an individual having a tumor. The kit may comprise oligonucleotides for specific detection of a hypermutated phenotype whether associated with treatment by an alkylating agent or not. In some embodiments, the kit further comprises reagents for carrying out amplification and detection using the included oligonucleotides, e.g., buffers, nucleic acid polymerase, reverse transcriptase, cofactors, dNTPs, detectable label, etc. Oligonucleotides can be used as primers for amplification of random or particular regions to be assessed for mutations. Sequencing of DNA or RNA is a useful technique for assessing mutational burden and expression profiles, respectively. The DNA to be sequenced can be directly obtained from a tumor sample or amplified from the DNA directly obtained from the tumor sample. RNA from the tumor can be sequenced directly or reverse transcribed and the resulting DNA sequenced. As discussed elsewhere, a tumor sample is any body fluid or tissue which is suspected of containing tumor cells or tumor DNA. Kits generally provide one or more reagents in separate containers all packaged in a single unified container. Often instructions will be included in the kit.

TCR signaling genes and other genes of enhanced inflammatory responses are known in the art. A collation of such genes may be found at the Innate database (InnateDB), for example. Such genes include COLEC12, IL17RA, JAM2, APP, TIAM1, HRH4, SERPIND1, IFNAR2, IFNAR1, IFNGR2, MAPK1, VPREB1, RNASE7, DDT, SLC14A1, ADORA2A, PSMB5, BCL2L2, IL25, XBP1, PSME1, PSME2, TCF4, MX2, MX1, LIF, CMA1, OSM, CTSG, GZMH, GZMB, LMAN1, ABCG1, TNFRSF11A, COCH, BCL2, SERPINB2, PSMA6, NFKBIA, CD226, ICOSLG, AIRE, NFATC1, FKBP3, ITGB2, ARF6, THBS1, DEFB1, DEFA6, DEFA4, ATL1, PDGFA, DEFA1, NCF4, CSF2RB, DEFA5, MCM3AP, IL2RB, C1QTNF6, RAC2, TMX1, DEFB105A, DEFB106A, MAEA, DEFB104A, DEFB103A, DEFB4A, PSMC6, LGALS1, CNIH, LTK, CARD11, GCH1, SOCS4, LGALS3, BLK, GTPBP1, PSMA3, GPR135, PDGFB, RPL3, LRPAP1, CCNDBP1, MSR1, ATF4, FGL1, AHR, PDIA3, MAPK8IP3, SPTB, GPX2, IL6, TNFRSF13C, MAX, LPL, B2M, CLNK, A4GALT, C1QTNT7, SCUBE1, BST1, CD38, FGFBP2, PROM1, LAP3, NOD1, TNFRSF10B, NINJ2, IL32, TNFRSF10C, TNFRSF10D, TNFRSF10A, MEFV, ENTPD5, MADCAM1, FKBP4, CREBBP, BSG, ADAMDEC1, BCL2L10, ADAM7, GLMM, DAP, PGF, ELMO1, AZU1, PRTN3, MAPK12, ELANE, MAPK11, CFD, NTF3, VWF, TLR10, TCF12, IL5RA, PSMA2, CD9, TLR1, ABCA7, TLR6, IL17D, TNFRSF1A, PTK2B, LTBR, CD27, TAPBPL, AQP9, CLU, CIITA, SCARA3, TSHR, SOCS1, LITAF, GPR65, LAG3, C1QTNF3, CD4, TNFRSF17, TNFRSF19, SCARF1, PTPN6, PSMC1, PSMD13, C1S, C1R, C1RL, NLRP6, IL7R, GADD45B, IFITM2, IFITM1, IFITM3, CD163, IKZF1, PPIB, CLEC4C, SIGIRR, C3AR1, IL17RE, CLEC4A, SPG21, S1PR4, IL17RC, PDCD7, LGMN, CLEC4E, IRF7, TXK, AICDA, TEC, DPP8, BAG4, KLRG1, OSMR, A2M, FYB, ITGAE, KLRB1, WASF3, C9, IRAK2, CLEC2D, IEI27, MAP2K1, CLECL1, CD69, PTGER4, KLRF1, CLEC2B, CLEC12A, MAP2K2, CLEC1B, SERPINA5, ADAM9, CD151, SERPINA3, CLEC7A, C7, EBI3, C6, OLR1, HRH1, MUC6, KLRD1, IDO1, MUC2, KLRC4, MUC5B, TCL1A, KLRC3, PPARG, KIT, BDKRB2, KLRC2, BDKRB1, KLRC1, ALOX15, TOLLIP, CCL28, RAF1, CXCL16, PSMB6, PLAT, FKBP6, FLT3, BCL7B, IKBKB, GP1BA, WARS, ITGA2, GZMK, IGF2, GZMA, FUT3, STAP1, TMPRSS11D, MLLT1, CD276, TRAF3, ART4, ARHGDIB, IL31RA, ALOX5AP, TNFAIP2, PML, C1QBP, IL6ST, NCF1, OPRK1, TUBB4A, TNESF9, CD70, TNESF14, C3, IL4R, NLRP1, ISLR, IL21R, CYP11A1, MAP3K1, VAV1, SEMA7A, NKIRAS1, CD81, MUC7, CSK, SIVA1, CCL26, CCL24, IL27, GPR132, GC, CLEC10A, SRCRB4D, RETN, FCER2, CD209, PTPN9, PDE7A, FGL2, CRH, AFP, CD19, CCR4, IL8, MAP2K7, CXCL6, CD36, PF4V1, CXCL1, SEMA3C, PF4, PPBP, CXCL5, CCL25, CXCL3, CXCL2, ART1, SPN, CD320, SEMA3A, RFXAP, MAZ, PSMA4, CD180, ACP1, CXCL9, ABCB1, CXCL10, CXCL11, CTSH, CAPRIN2, RPL7, TPO, BCL2A1, MYD88, MAPK3, CXCL13, LY96. CD68, IL16ANXA3, IL7, ITGAL, CX3CR1, CCR8, ICAM1, ICAM4, ICAM5, ENTPD3, ICAM3, TFPI2, BCL7C, CTNNB1, ITGB1BP1, WWP1, ALOX15B, VKORC1, VIPR1, ADAM17, ALOX12B, NKTR, ALOXE3, TRIM22, RIPK2, ILF3, PYCARD, IRAK4, CCBP2, ITGAM, TAC1, ITGAX, MAPK10, ITGAD, TNFSF11, RUNX1T1, TMED1, PTPN13, AFF1, GEM, HAPLN3, COL4A3BP, VDR, EPOR, SPP1, TPT1, RHCG, F2RL2, F2R, F2RL1, CCR9, CXCR6, XCR1, CCR1, CCR3, MMRN1, CCR2, AZGP1, CCR5, CPB2, ZNF3, CCRL2, LTF, HPGDS, NOD2, ST8SIA2, JUNB MAP2K4, PRDX2, CALR, ADM, TFR2, EPO, NFKB1, DCSTAMP, MT2A, CAMP, PLXNB1, TNERSF13B, MUC3A, RFX1, IL27RA, CYSLTR2, MUC12, ATF1, MUC17, SERPINE1, CD97, PSMA1, CCL22, CX3CK1, AIMP1, CCL17, EMR3, TNFRSF11B, ACVR1B, EMR2, CASP6, CFI, CASP14, HAS2, PSMC2, ERAP1, PGLYRP2, RNF112, CDH5, MST1, MAP2K3, TRAIP, SLC26A4, MST1R, LAMB1, LGALS9, F2RL3, NOS2, ITGB7, TG, ANXA5, ELMO3, DDA1, MUC15, TNFAIP1, TSLP, DEFB125, SARM1 DEFB126, BST2, DEFB127, DEFB129, FOXN1, IL2, IL21, PTK2, CISH, JAK3, IL12RB1, TRAF4, PSMB10, CFTR, GPR84, LY6D, ITGA5, JUND, NFATC3, LY6E, LY6H, EIF3M, TLR9, FKBP8, ITGA7, CD59, PSMF1, HAS3, TSTA3, WASL, CD63, IL15, NFAT5, CSF2RA, GYPS, FKBP1A, RFXANK, CD44, LEP, GYPA, IL3RA, IKZF4, ABCE1, ERBB3, PBX4, PRKCD, TRAF6, RAG1, PSMD11, SIRPB1, IRF5, IL17RB, HSF1, CCL2, CCL7, CCL11, CCL8, CCL13, CCL1, CD99, LRBA, CD82, IL23A, STAT2, UBE2H, XG, TONSL, CHST4, IL17RD, IL3, CSF2, TLR2, PSMD7, FGB, F2, FGA, STAT6, IRF1, FGG, LRP1, IL5, IL13, IL4, XDH, PTN, CLEC3A, PSMC3, NLRC4, KANK1, C1QTNF4, TBXAS1, HAMP, MAG, CD22, PTPRJ, TLR7, FFAR2, TLR8, TCF7, AVPR1A, HMGB2, EIF2AK2, TBK1, CAMLG, IRF8, KEL, IRAK3, MED1, CXCL14, IL9, CASP2, SLC7A5, IFNG, HCST, IL26, TYROBP, IL22, PROS1, PIGA, ERBB2, ZFPM1, GPR183, ATL2, IL17C, IRF2, IKZF3, CASP3, PRG3, PRG2, PSMD3, SERPING1, ATRN, CSF3, CBFA2T3, LYZ, JAK2, DCBLD2, EGR 1, TLR3, CD274, KLKB1, PDCD1LG2, F11, SIGLEC1, MZB1, CCR7, TSPAN8, GIMAP8, GIMAP7, GIMAP4, GIMAP6, GIMAP5, NFKBIZ, ALCAM, CBLB, HBEGF, PSMD8, MS4A6A, CD47, MS4A3, MS4A2, MS4A4A, MS4A6E, MS4A7, MS4A5, MS4A1, TRAT1, CD14, IK, MS4A12, MS4A8B, MAP4K1, PTGDR2, CD96, LGALS4, CD6, CD5, NFKBIB, CD200, PRNP, TNFSF13B, BTLA, CD200R1, IL28B, IL28A, IL29, IL15RA, NFIB, STAT5B, IL2RA, STAT5A, MCFD2, STAT3, FTH1, MNX1, EPCAM, PSMC4, FOXN2, CD80, SOCS2, CRADD, CCR10, NR3C1, PSME3, SLC3A2, IFI35, F7, F10, CD86, PROZ, KPNA1, GATA3, AXL, TGFB1, BCL11A, IL17B, MLLT3, REL, ARL1, CEACAM5, CEACAM6, CSF1R, FKBP2, PDGFRB, CD79A, BAD, IL1RAPL1, IFNB1, IFNW1, IFNA21, CD74, SLC4A1, POU2F2, IFNA10, IFNA16, ITGA2B, ITGB5, MUC13, IFNA5, PAFAH1B3, IFNA6, HSP90B1, IFNA2, IFNA8, CAMK1D, IFNA1, IFNE, CEACAM1, SPARC, C1QL1, CEACAM8, MAP3K14, CRHR1, MXD1, CD177, MAP4K2, HAVCR2, CMKLR1, SART3, ITK, TGFA, IFNK, PLAUR, SELPLG, GP9, ADAM19, CD207, IRF4, XK, EBF1, IL12B, C1QTNF2, TBX21, MVK, SP2, PVR, BCL3, HMMR, BCAM, SERPINB9, SKAP1, PVRL2, BAG1, RELB, CCRL1, LCP2, TF, RIPK1, CD3EAP, RELA, MAPKAPK5, TAC4, EFEMP2, CTSW, ITGA3, TACR1, BANF1, OAS1, OAS3, OAS2, PGLYRP1, PACS1, HRH2, REG3A, PTGIR, TCF7L1, GGCX, F13A1, LY86, HRK, TOB1, C5AR1, THBD, GNLY, NOS1, KPTN, PRELID1, F12, PLA2G4C, CD8A, MMD, PLSCR4, CARD8, CST4, CST2, SIGMAR1, IL11RA, CP, CST7, EPX, MLLT10, GCNT2, MPO, CCL19, CCL21, HNF1A, FUT1, TCIRG1, OASL, BAX, CANX, FTL, ELK1, EDN1, CCND1, P2RY1, PSMD9, MME, FADD, CLIP1, SSX6, CD37, ZAP70, SSX5, SSX1, DEFB118, SSX9, CD72, DEFB119, SSX3, CD83, FLT3LG, DEFB123, PTX3, HM13, IL18BP, FCGRT, MRC2, IRF3, IL12A, MAP3K3, AFF3, ID1, B3GALNT1, BCL2L1, ATP6V0A2, WAS, PSMC5, IL4I1, RELT, MAP4K4, SIGLEC11, SERPINI2, SCARB1, ABI1, IL1R2, IL1R1, IL1RL2, IL1RL1, IL18R1, IL18RAP, CD79B, POU3F3, HCK, SPIB, ICAM2, ARRB1, CLEC11A, SFSWAP, GNE, PRKRIR, TNFSF10, APOH, B3GNT6, PAX5, PSMD12, TDP2, SIGLEC9, SIGLEC7, CD33, SIGLECL1, NKG7, SIGLEC10, SIGLEC8, GAB2, SIGLEC6, ZNF175, SIGLEC5, BPIFA1, FOXP3, HAS1, FPR1, FPR2, FPR3, IL1A, MAP2K6, IL1B, IL37, CBFA2T2, IL36G, TRIM38, IL36A, MAP3K8, IL36B, IL36RN, IL1F10, IL1RN, ZEB1, CTSC, CD300E, HFE, CD300LF, NLRP12, PSMD2, MARCO, OSCAR, ITCH, THPO, FUT4, ITGB1, LILRB3, LILRB5, LILRB2, LILRA5, NRP1, LAIR1, GYPC, NCOA6, ITGB4, LILRA1, SSX8, LILRB1, LILRB4, AHSG, SSX7, KIR2DL1, FETUB, SSX7, MAP3K2, HRG, BIRC3, KNG1, BIRC2, PROC, BTN3A2, ADIPQQ, ST6GAL1, BTN2A2, MASP1, BTN3A1, TRPC4AP, BCL6, BTN3A3, KIR2DL4, CREM, PROCR, BTN2A1, BTN1A1, KIR3DL1, CASP5, CASP1, FCAR, IL1RAP, NCR1, NLRP2, PRSS16, ATM, GP5, BIRC5, IL11, SOCS3, MUC4, POU2AF1, CYTH1, LGALS3BP, TFRC, CXCR4, C1QINF1, NLRP9, HNMT, IL18, MFI2, CARD14, NCAM1, CXCL12, 8-Mar, AATK, TNFAIP6, GNAQ, TGIF2, SLA2, PAFAH1B2, LY75, IL10RA, CD7, SECTM1, MAPK8, MOG, TANK, CD3E, CD3D, FOXK2, CD3G, SAMHD1, DPP4, MLL, HLA-F, CXCR5, SRC, EDA, CBL, MCAM, THY1, PVRL1, BPI, MBL2, LBP, CRTAM, HSPA8, IL2RG, DAPK1, CTSL1, ITGA6, MAFB, SPA17, SEMA4D, WIPF1, SYK, NFIL3, TIRAP, ETS1, PRKRA, DDR1, ABCF1, CXCR3. PPP1R10, SRGN, NINJ1, HNF4A, ITGA4, TUBB, ADA, IER3, ITGAV, TFPI, GULP1, PI3, HLA-C, SLPI, PRF1, MICA, STAT1, STAT4, MICB, DDX39B, NEKBIL1, HSPD1, LST1, CYSLTR1, NCR3, TRIM14, AIF1, AOX1, CFLAR, CASP10, GPANK1, CASP8, LY6G5C, ABHD16A, MMP9, LY6G6E, LY6G6C, PLAU, CD40, ADK, ELMO2, CD28, CTLA4, ICOS, HSPA1L, HSPA1A, HSPA1B, NRP2, ABCA1, BTK, CFB TAL2, SKIV2L, IKBKAP, PREX1, ERBB4, IKZE2, SFTPA2, SFTPA1, SFTPD, FN1, FKBPL, ANXA11, AGER, PBX2, NOTCH4, LPAR1, BTNL2, HLA-DRA, CXCR2, CXCR1, HLA-DRB5, CEBPB, HLA-DRB1, PTPN1, SLC11A1, IL1RAPL2, HLA-DQA1, HLA-DQB1, NFATC2, TAP2, PSMB8, TAP1, TSC22D3, PSMB9, HLA-DMA, FAS, HLA-DOA, PSMD10, HLA-DPA1, IFIT2, IFIT3, IFIT1, IFIT5, RXRB, TNFSF8, TNC, CCL20, TRIM32, DAXX, TLR4, SP110, BAK1, IL13RA2, PSMD1, PSMD5, TRAF1, C5, IL13RA1, INPP5D, DGKD, ENTPD1, BLNK, NKRF, SCUBE3, PTGS1, DEF6, PSMA7, PPARD, CXCR7, HRH3, FKBP5, ISG15, TNFRSF18, TNFRSF4, MAPK14, MAPK13, PSMB7, XIAP, PBX3, PDCD1, SH2D1A, DIDO1, APLN, ABCC2, TNFRSF14, TREML1, TREM2, ENG, TREM1, NCR2, PTCRA, CD40LG, F9, NFKB2, MAGEC1, TNFRSF9, SET, VEGFA, CD99L2, MASP2, PTGES, MXI1, PDCD4, NFKBIE, ABL1, BCAP31, NPPA, TCF7L2, HABP2, TNFRSF8, TNFRSF21, CASP7, CD2AP, TNFRSF1B, RHAG, CRISP3, IL17A, IL17F, IRAK1, GBGT1, ABO, TIAL1, BAG3, PADI4, FCN2, FCN1, DMBT1, CTAG1B, CTAG2, PAEP, F8, IKZF5, NOTCH1, CD109, IL9R, HTR6, PLA2G2A, TRAF2, PLA2G2D, C8G, FUT7, ENTPD2, DOCK 1, IRAK1BP1, ADAM8, C1QA, C1QC, C1QB, NT5E, CNR2, IL22RA1, IL28RA, RHD, RHCE, CASP8AP2, MAP3K7, PAFAH1B2, POU3F2, CD52, SYTL1, FCN3, WASF2, IFI6, CD164, PTAFR, WASF1, YTHDF2, OPRD1, TXLNA, LCK, YARS, HSF2, PSMB2, CSF3R, POU3F1, CTGF, VNN2, PABPC4, MAP3K5, IL20RA, IL22RA2, IFNGR1, TNFAIP3, YBX1, MPL, DPH2, TAB2, RAET1E, ULBP2, ULBP1, RAET1L, ULBP3, PRDX1, OPRM1, TAL1, SOD2, IGF2R, PLG, MAP3K4, CCR6, MLLT4, C8A, C8B, JUN, PSMB1, PDCD2, JAK1, LEPR, IL23R, IL12RB2, IFI44, BCL10, GBP3, GBP1, GBP2, GBP4, GBP5, F3, VCAM1, VAV3, PSMA5, GSTM1, CSF1, CD53, CHIA, ADORA3, PTPN22, NGF, CD58, CD2, CD101, VTCN1, CD160, FCGR1A, MCL1, CTSS, ARNT, PSMD4, PSMB4, PGLYRP3, PGLYRP4, S100A9, S100A12, S100A8, ILF2, IL6R, ADAR, MUC1, DAP3, RHBG, NTRK1, CD5L, CD1D, CD1A, CD1C, CD1B, CD1E, MNDA, IFI16, AIM2, FCER1A, CRP, SLAMF8, SLAMF6, CD84, SLAMF1, CD48, SLAMF7, LY9, CD244, F11R, FCER1G, FCGR2A, FCGR3A, FCGR3B, FCGR2B, FCRLA, PBX1, POU2F1, CD247, XCL2, XCL1, F5, SELP, SELL, SELE, FASLG, TNFSF4, SERPINC1, MR1, NCF2, HMCN1, PTGS2, PLA2G4A, RGS1, CFH, CFHR3, CFHR2, CFHR4, F13B, PTPRC, PTPN7, ADORA1, ELK4, MAPKAPK2, IL10, IL19, IL20, IL24, PIGR, C4BPB, C4BPA, CD55, CR2, CR1, CR1L, CD46, CD34, IRF6, TRAF5, TLR5, WNT3A, LGALS8, NLRP3, GP1BB, C2, BAG6, HLA-E, C4A, HCP5, TNFRSF25, MUC5AC, HLA-DPB1, IFNA7, ITGA1, IRF9, CCL27, LTB4R2, LTB4R, UBD, KLRK1, DDAH2, LAT, GPSM3, PTPRCAP, CHUK, DARC, KIR3DL2, EBF2, CEBPD, TIAF1, IFI30, CKLF, KIR2DS4, HLA-G, HLA-A, IFNA4, IFNA17, IFNA14, IFNA13, FILA-B, PRRC2A, TNF, C4B, LTA, LTB, HLA-DQB3, HLA-DQA2, HLA-DQB2, TAPBP, IK, ORM1, ORM2, NTF4, C1QTNF5, IFNAR2, IL10RB, MIF, EIF6, DEFA3, TNFRSF6B, LY6G5B, LY6G6D, HLA-DOB, TAP2, PSMB9, HLA-DMB, HLA-DMB, TICAM2, KIR3DL2, TLR9, TNFSF12, LYN, TNFRSF13B, C5orf20, GYPB, SSX2, TM4SF2, PDCD6, CNTF, CFHR1, FCGR2C, LILRA4, LILRA2, KIR2DL3, KIR3DL3, KLRC2, PSMA1, LY6G6E, KLRK1, ITGB3, CLEC5A, PSMD9, HP, ITGB3, VIKORC1, TRIM34, HPR, SIGLEC11, SIGLEC5, SPIB, IKBKE, CCL3, and IKBKG.

Definitions—The following definitions are provided to facilitate understanding of the disclosure, and to provide illustrative examples for use of the terms.

As used herein, the terms "a", "an", and "the" mean "one or more", unless the singular is expressly specified (e.g., singular is expressly specified, for example, in the phrase "a single mutation").

As used herein, the terms "first" and "second" are for purposes of distinguishing between two compounds, or between two compositions, or between two steps in a process, as will be clearer from the description.

As used herein, "therapeutic effect," "clinical benefit," and "response," with respect to following treatment, are used to refer to a beneficial response to treatment. For example, assessment of a beneficial response may comprise (a) an immune-related response, as known to those skilled in the art as an immune-related complete response or an immune-related partial response relative to total tumor burden; (b) traditional overall objective response rate using the appropriate response assessment criteria known to those skilled in the art and depending on the type of cancer treated (e.g., for lymphoma, see Cheson et al., 2014, *J. Clin. Oncology* 32 (27):3059-3067; for solid nonlymphoid tumors, Response Evaluation Criteria In Solid Tumors (RE-CIST)), which may include but is not limited to, an increase in the proportion of surviving, survival probability, progression free survival, or tumor regression; or reduced rate of tumor growth or metastasis.

As used herein, the terms "cancer" or "tumor" refer to all types of cancer, neoplasm or malignant tumors found in mammals (e.g., humans), including solid nonlymphoid tumors, leukemia, lymphomas, carcinomas, and sarcomas. The tumor cells in a tumor may express CD155 on their surfaces ("CD155$^+$"), may lack detectable expression of CD155 (CD155$^-$) or the tumor may comprise a mixture thereof (some cells being CD155$^+$, some cells being CD155$^-$).

As used herein, the term "individual" is used herein to refer to a mammal, preferably a human. A human in need of a method described herein is an individual having a tumor or is suspected of having a tumor.

As used herein, the term "tumor mutational burden" or "tumor mutational load" refers to a quantitative representation of the total number of mutations per a coding area of a tumor genome ("total variants"). Using genomic sequencing data and bioinformatics, somatic missense mutations detected from analyzing samples comprising tumor from a cohort of individuals having the same type of tumors may be used to calculate an average of such mutations, which may then be used as a representative metric for tumor mutational burden. If a distribution of log-transformed somatic missense mutation count follows an approximately normal distribution, the cohort's mean number of missense mutations may serve as a threshold to separate individuals whose tumors have a low mutational burden or low mutational load (e.g., a number of missense mutations less than the cohort's mean or median number of missense mutations) from individuals whose tumors have a high mutational burden or high mutational load (e.g., a number of missense mutations greater than the cohort's mean number of missense mutations). Depending on the cohort of individuals studied (reference population), the tumor type used for determination of tumor mutational burden, and in relation to a specific agent considered for treating the individual, illustrative examples of a high mutational burden may comprise greater than or equal to 1.9 or 1.5 total mutations per megabase for recurrent glioblastoma; or greater than 12 mutations per megabase (e.g., as described for a cohort of individuals having colon and endometrial cancers); or 17 or more mutations per megabase (e.g., as described for a cohort of individuals having colorectal carcinoma); and may reach upwards to hundreds or more mutations per megabase. In another example, in a study of response to checkpoint inhibitors in a cohort of individuals having melanoma, a higher or high mutational burden was greater or equal to 20 mutations per megabase, whereas low or intermediate mutational burden was less than or equal to 5 mutations per megabase (Goodman et al., 2017, *Mol. Cancer Ther.*, 16(10: 2598-2608).

As used herein, the term "kit" refers to a packaged combination of components, such as reagents for detecting mutations; and may further comprise one or more components to facilitate reconstitution, administration, delivery, or use of the contents of the kit. In some embodiments, and for detecting specific mutations of interest (see, e.g., FIG. 6), the kit may further comprise oligonucleotides (e.g., probes and/or primers) specific for the mutated sequence (e.g., able to distinguish from a corresponding wild-type sequence). In some embodiments, the kit comprises reagents for amplification and detection of specific mutations of interest.

As used herein, the term "administering" or "administer" refers to giving an individual an agent described, introducing an agent into an individual (e.g., into the body of the individual), and recommending or prescribing to an individual a therapeutic regimen comprising an agent described.

As used herein, the terms "tumor sample" or "sample from an individual" or "an individual's tumor" refer to body fluid, tissue, or combination thereof which is isolated from an individual and which is suspected of containing tumor cells or nucleic acid molecules (RNA and/or DNA) originating from tumor. For example, the sample may be tissue biopsy, fluid biopsy, blood, plasma, serum, spinal fluid, urine, synovial fluid, or body secretions; or nucleic acid molecules partially purified or purified therefrom.

"Testing" is used to refer to a laboratory procedure in which a chemical, biochemical, or enzymatic reaction is performed on a sample to transform a starting material to a product.

Expression levels are determined by quantitatively assisting expression products of particular genes. This can be accomplished by sequencing and tallying RNA molecules, hybridizing RNA molecules to arrays of probes, or using a technique such as SAGE (serial analysis of gene expression). These are just exemplary of techniques which may be employed. As in determining high and low levels of tumor mutational burden, high and low levels of expression of certain genes and classes of genes can be accomplished by comparison to a reference population having similar tumors and determining median or mean level of expression. Quantitative determination of particular proteins may similarly be used for this assessment.

Detection refers to the machine or human collection of results and/or evaluation of results of a testing reaction. Determination refers to finding of a particular result of a testing reaction, for example, where more than one result can occur, identifying which such result has occurred.

As used herein, the terms "immune checkpoint inhibitor" or "checkpoint inhibitors" refer to any one or more of a molecule, composition or antibody that disrupts the inhibitory interaction of immune cells and tumor cells. For example, T cells and/or macrophages may be tolerized so as not to respond in an anti-tumor immune response. A checkpoint inhibitor is aimed at inhibiting such interaction so as to allow the immune cells to respond in an anti-tumor immune response. Checkpoint inhibitors are known to include but are not limited to anti-PD-1 antibody, anti-PD-L1 antibody, anti-CTLA4 antibody, anti-LAG-3 antibody, anti-CD47 antibody, and/or anti-TIM-3 antibody. Approved checkpoint inhibitors in the U.S. include atezolizumab, ipimilumab, pembrolizumab, and nivolumab. Additional checkpoint inhibitors which may be used include avelumab, durvalumab, and spartalizumab. The inhibitor need not be an antibody, but can be a small molecule or other polymer. If the inhibitor is an antibody it can be a polyclonal, monoclonal, fragment, single chain, or other antibody variant construct. Inhibitors may target any immune checkpoint known in the art, including but not limited to, CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, CD47, A2aR, and the B-7 family of ligands. Combinations of inhibitors for a single target immune checkpoint or different inhibitors for different immune checkpoints may be used. Additionally, CSF-1R blockade may be used in combination or as an alternative to immune checkpoint inhibitor(s), to ensure generation of potent and sustained immunity that effectively eliminates distant metastases and recurrent tumors. Antibodies specific for CSF-1R or drugs that inhibit or blockade CSF-1R may be used for this purpose, including but not limited to imactuzumab and AMG820.

Inducers of innate immunity may be used in the invention with or in place of PVSRIPO. These include without limitation imiquitnod, polyinosinic-polycytidylic acid stabilized with polylysine and carboxymethylcellulose (poly-ICLC), Stimulator of interferon genes (STING) agonist, Toll-like receptors (TLR) agonist, and cytokine-inducible $SH_2$-containing protein (CISH).

Other oncolytic viruses may be used in conjunction with or in place of PVSRIPO. These include without limitation Talimogene laherparepvec (T-VEC), vaccinia virus, vesicular stomatitis virus, reovirus, senecavirus, and Semliki Forest virus.

A more complete understanding can be obtained by reference to the following specific examples, which are provided for purposes of illustration only, and are not intended to limit the scope of the invention.

EXAMPLES

Example 1

Treatment with an Immunotherapeutic Agent Comprising PVSRIPO

PVSRIPO is the live-attenuated poliovirus type 1 (Sabin) vaccine with its cognate internal ribosome entry site (IRES) replaced with that of human rhinovirus type. PVSRIPO's foreign IRES causes neuronal incompetence that ablates neurovirulence (see, FIG. 1). PVSRIPO tropism is determined by CD155, a cell adhesion molecule and high affinity ligand for T cell immunoreceptor with immunoglobulin and ITIM domains. In solid tumors, CD155 is broadly upregulated on malignant cells, and is also expressed on antigen presenting cells, e.g. dendritic cells and tumor-associated macrophages. PVSRIPO infection of neoplastic cells results in lethal cytotoxicity, induces innate antiviral interferon responses, and elicits immune cell invasion of the tumor. PVSRIPO causes chronic, sublethal infection of antigen presenting cells, elicits sustained proinflammatory cytokine responses, and stimulates antigen presentation/T cell co-stimulation. Tumor cytotoxicity, combined with interferon-dominant activation of APCs and the strong inflammatory response to poliovirus counters tumor-inherent immunosuppression and instigates antitumor immunity.

A Phase I clinical trial was conducted in individuals with recurrence of histopathology-confirmed, WHO grade IV malignant glioma using PVSRIPO alone as the therapeutic agent. For confirmation of viable malignant glioma and for genomic analyses of tumors, a stereotactic biopsy was performed prior to administration of PVSRIPO. Magnetic resonance imaging (MRI) was obtained at screening, within 4 hours after completion of administration, 4 and 8 weeks after administration, followed by every 8 weeks for one year, and afterward at an interval selected by the treating physician. Imaging allowed for tumor measurements including change in size from baseline and nadir, assessment of disease status, and other information for determining responsiveness to treatment. Sixty-one patients with recurrent WHO grade IV malignant glioma were treated on study. The dose-escalation phase of the study included one patient each on dose levels 1-3, two patients on dose level 4, and four patients on dose level 5 for dose levels). For the dose-expansion phase, 6, 31 and 15 patients were treated on dose levels 2, −1, and −2, respectively (see, Table 1).

TABLE 1

| Dose Level | TCID50 |
|---|---|
| −2 | $1.0 \times 10^7$ |
| −1 | $5.0 \times 10^7$ |
| 1 | $1.0 \times 10^8$ |
| 3 | $1.0 \times 10^9$ |
| 4 | $3.3 \times 10^9$ |
| 5 | $1.0 \times 10^{10}$ |

PVSRIPO was administered after tumor resection and directly into the tumor. Convection-enhanced delivery was used to infuse PVSRIPO intratumorally. An implanted catheter was used to infuse PVSRIPO at a delivery rate of 500 µL/hr, with 3 mL being the total amount of the inoculum delivered to the individual. The results of the Phase I trial are summarized in Table 2 (followed up to Mar. 20, 2018), wherein individuals treated with PVSRIPO are compared to historical controls. As shown in Table 2 and FIG. 2, overall survival for individuals treated with PVSRIPO is significantly improved, particularly at 2 years and beyond, as compared to historical controls.

TABLE 2

PVSRIPO dose escalation patients vs Historical Control: Overall survival

| Group | Total | # Failed | 12-month survival (95% CI) | 24-month survival (95% CI) | 48-month survival (95% CI) | 60-month survival (95% CI) |
|---|---|---|---|---|---|---|
| PVSRIPO DL 1-5 | 15 | 12 | 60.0% (31.8%, 79.7%) | 20.0% (4.9%, 42.4%) | 20.0% (4.9%, 42.4%) | 20.0% (4.9%, 42.4%) |
| Historical controls | 104 | 103 | 45.2% (35.5%, 54.4%) | 13.5% (7.8%, 20.7%) | 1.9% (0.4%, 6.1%) | 0% |

Figure 2:
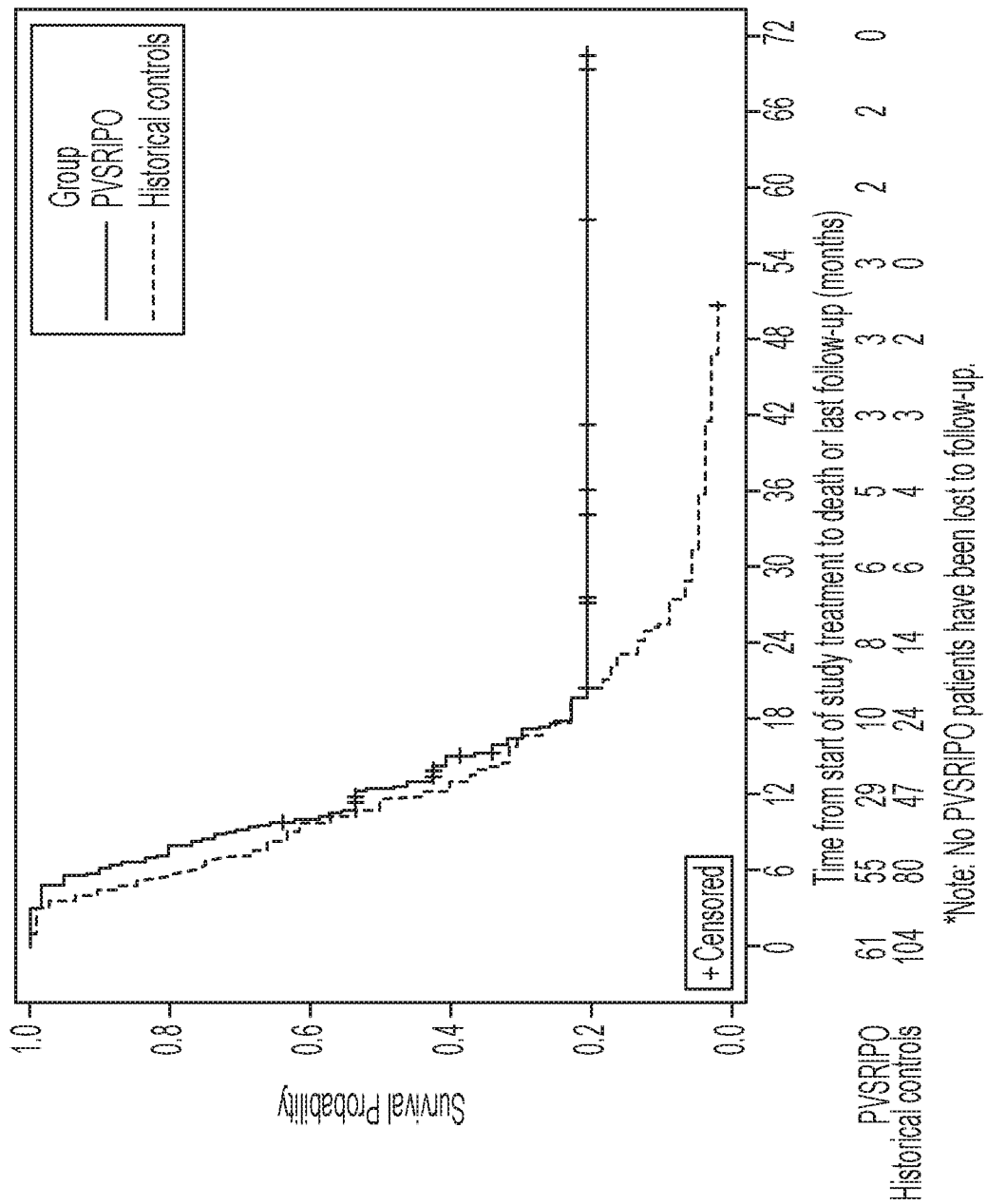
FIG. 2 is a Kaplan-Meier curve of overall survival for historical controls (dashed line) as compared to individuals treated with the various doses of PVSRIPO (solid line; "PVSRIPO") with the y-axis as overall survival ("Survival Probability") and the x-axis as the number of months. These results are from a phase I study of PVSRIPO for recurrent glioblastoma. The overall survival shown is as of Mar. 20, 2018. These data were previously published in New England Journal of Medicine, 379:150-161, 2018.

Despite aggressive surgery, radiation therapy, and multi-agent chemotherapy, survival after a new diagnosis of WHO grade IV malignant glioma is usually <20 months, and individuals with recurrence usually survive <12 months. As shown in FIG. 2, the Kaplan-Meier overall survival curve of all 61 individuals treated with PVSRIPO versus the historical controls revealed increased long-term overall survival with a higher proportion of individuals treated with PVSRIPO alive at 24 months. 48 months, and 60 months. The overall survival of individuals treated with PVSRIPO reached a plateau and separated from the historical control group beginning at 24 months, with a 24-month overall survival of 20.0% (95% CI: 4.9%, 42.4%), while the historical control overall survival continued to decline with 24-month overall survival of 13.5% (95% CI: 7.8%, 20.7%), and 48-month overall survival of 1.9% (95% CI: 0.4%, 6.1%). Two individuals maintained complete responses >64.1 months after treatment with PVSRIPO. Three individuals showed stable to partial radiographic responses for 60 months, 34 months and 26 months, respectively.

Example 2

Genetic Analyses: Tumor Mutational Burden and a Hypermutated Phenotype Associated with Treatment by an Alkylating Agent From samples obtained from a cohort of individuals treated in the study described in Example 1, DNA libraries for whole-exome sequencing were constructed using a commercially available kit. Whole-exome sequencing was performed using standard reagents and methods known in the art. For determining tumor mutational burden, the number of somatic mutations was detected; with alterations likely or known to be bona fide oncogenic drivers and germline polymorphisms were excluded. Tumor mutational burden was measured in mutations per megabase (Mb). Tumor mutational burden levels were divided into two groups: low mutational burden (<1.9% total variants per Mb), and high mutational burden (≥1.9 total variants per Mb). Analyses on total variants (Mb) were conducted on 3 sets of data as follows.
1) 39 individuals treated with PVSRIPO with a tumor sample obtained regardless of time point (1 sample/per individual).
2) 31 individuals treated with PVSRIPO with a tumor sample obtained pre-treatment with PVSRIPO (1 sample/per individual)
3) 18 individuals treated with PVSRIPO with a tumor sample obtained immediately prior to treatment with PVSRIPO.

Figure 3:
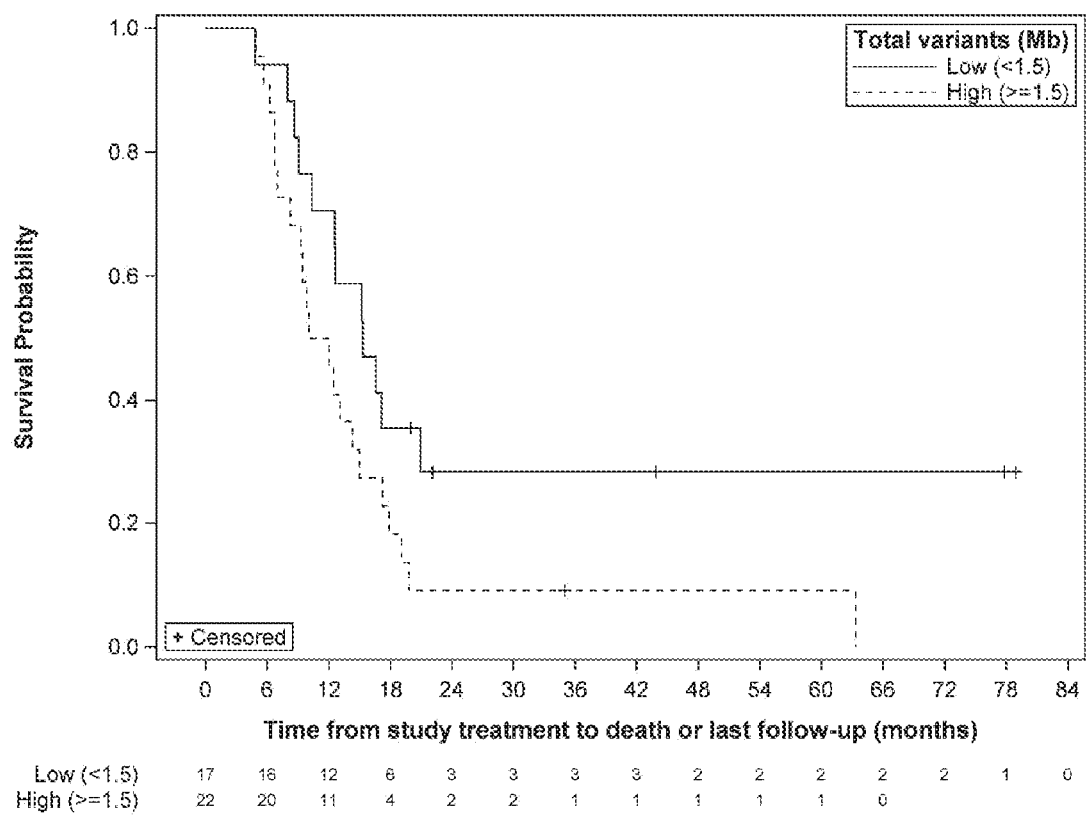
FIG. 3 shows overall survival and total variants (Mb) as of Dec. 5, 2018 (1 sample/patient; including the tissue sample from immediately prior to PVSRIPO if available, otherwise using the sample before and closest to PVSRIPO administration, or the earliest available sample which includes some post-PVSRIPO and autopsy samples). Patients with low variants are shown with the solid line. Patients with high variants are shown with a dotted line.

For 39 individuals treated with PVSRIPO with a tumor sample regardless of time point (1 sample/per individual), and as shown in Table 3 and FIG. 3, overall survival ("OS") for individuals having tumor in which detected was a low tumor mutational burden (<1.9 total mutations/Mb) was significantly better than individuals having tumor in which detected was a high tumor mutational burden (≥1.9 total mutations/Mb). For individuals having tumor with low tumor mutational burden, median OS was 16.5 months (95% CI: 10.4, 19.8), whereas median OS was 9.6 months (95% CI 6.7, 14.3) for individuals having tumor with high tumor mutational burden (Log-rank p=0.049). Cox model analysis was also conducted to assess the impact of total mutational burden on survival. The hazard ratio for individuals with tumor having high tumor mutational burden (≥1.9) was 2.06 (95% CI: 0.99, 4.31; p=0.054). The Cox analysis indicates that as total tumor mutational burden increases, individual survival decreases hazard increases).

TABLE 3

| | | Overall survival by total variants (N = 39; 1 sample/individual*) | | | | |
|---|---|---|---|---|---|---|
| Group | Total | Median survival in months (95% CI) | 12-month survival (95% CI) | 24-month survival (95% CI) | 48-month survival (95% CI) | 60-month survival (95% CI) |
| Low (<1-9) | 21 | 16.5 (10.4, 19.8) | 71.4% (47.2%, 86%) | 25.3% (8.3%, 46.9%) | 25.3% (8.3%, 46.9%) | 25.3% (8.3%, 46.9%) |
| High (≥1.9) | 18 | 9.6 (6.7, 14.3) | 44.4% (21.6%, 65.1%) | 12.7% (2.2%, 33%) | 12.7% (2.2%, 33%) | 12.7% (2.2%, 33%) |

Log-rank p = 0.049

*Note:

Using sample from immediately prior to PVSRIPO if available; otherwise using sample before and closest to PVSRIPO administration, or the earliest available sample which includes some post-PVSRIPO and autopsy samples.

Surprisingly, and in striking contrast to studies of tumor mutational burden and response to studies of tumor mutational burden and response to checkpoint inhibitors, a lower tumor mutational burden was associated with a therapeutic effect and clinical benefit after treatment with PVSRIPO, as compared to a high tumor mutational burden.

Figure 4:
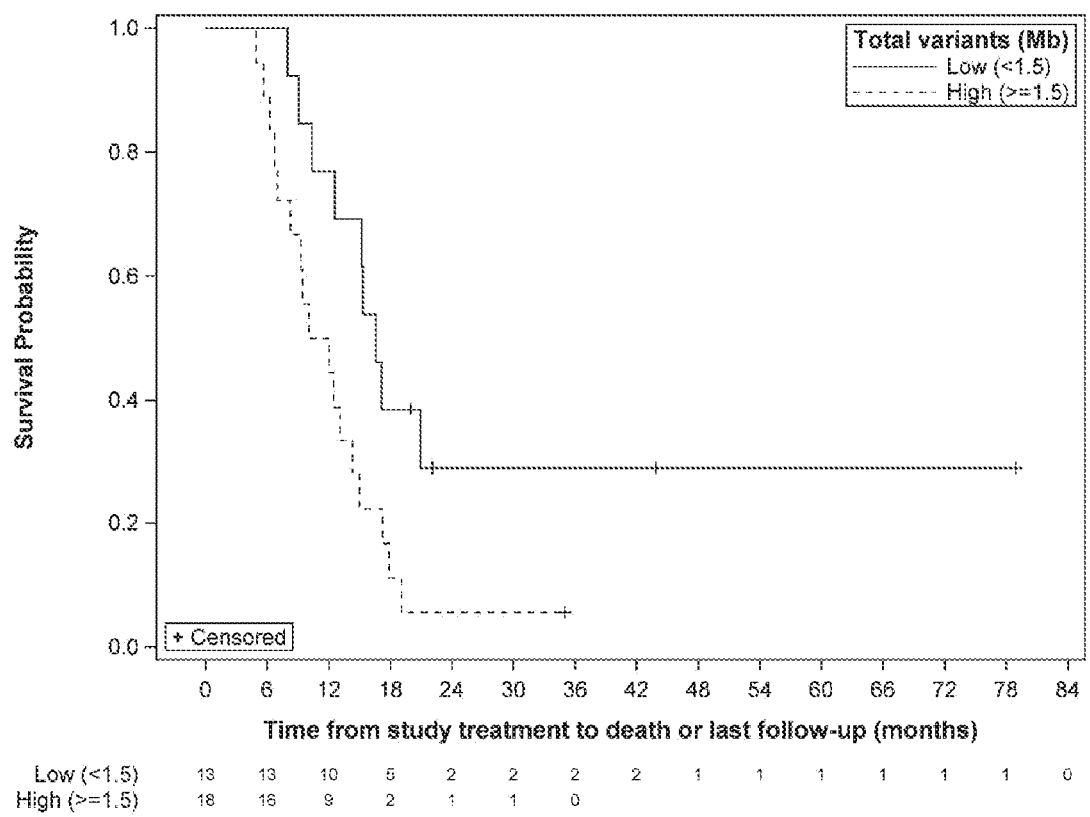
FIG. 4 shows overall survival and total variants (Mb) as of Dec. 5, 2018 (1 sample/patient; including the tissue sample from immediately prior to PVSRIPO if available, otherwise using the sample before and closest to PVSRIPO administration). Patients with low variants are shown with the solid line. Patients with high variants are shown with a dotted line.

For 31 individuals treated with PVSRIPO and with a tumor sample obtained at any time point prior to PVSRIPO administration (1 sample/per individual), as shown in Table 4 and FIG. 4, survival for individuals with tumor having low tumor mutational burden (<1.9 total mutations/Mb) was significantly better than individuals with tumor having high tumor mutational burden (≥1.9 total mutations/Mb). For individuals with tumor having low mutational burden, median OS was 16.5 months (95% CI: 10.4, ∞), whereas median OS was 9.4 months (95% CI 6.3, 14.3) for individuals having tumor with high mutational burden (Log-rank p=0.018). Cox model analysis was also conducted to assess the impact of total mutational burden on survival. The hazard ratio for individuals with high tumor mutational burden (≥1.9) was 2.64 (95% CI: 1.14, 6.12; p=0.023). The Cox analysis indicates that as total tumor mutational burden increases, individual survival decreases (i.e. hazard increases).

In striking contrast to studies of tumor mutational burden and response to studies of tumor mutational burden and response to checkpoint inhibitors, a lower tumor mutational burden was associated with a therapeutic effect and clinical benefit after treatment with PVSRIPO, as compared to a high tumor mutational burden.

Figure 5:
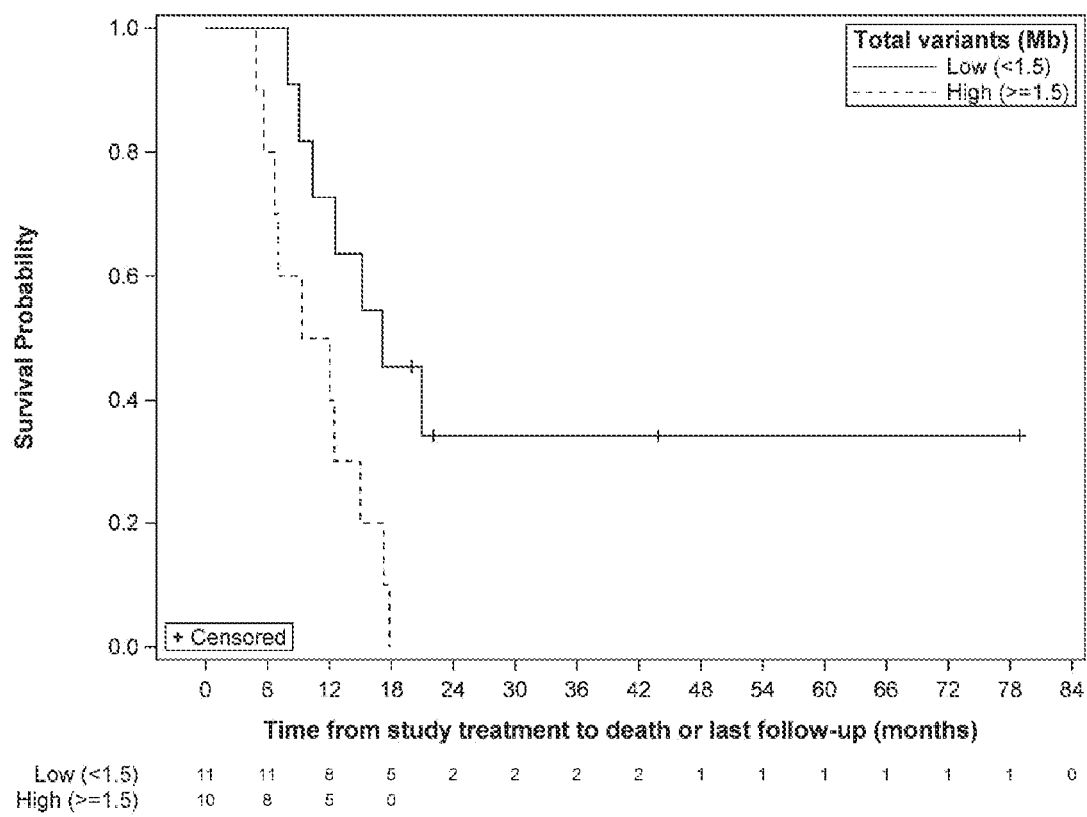
FIG. 5 shows overall survival and total variants (Mb) as of Dec. 5, 2018 (1 sample/patient; all tissue samples immediately prior to PVSRIPO). Patients with low variants are shown with the solid line. Patients with high variants are shown with a dotted line.

For 18 individuals treated with PVSRIPO with a tumor sample obtained immediately prior to PVSRIPO administration, and as shown in Table 5 and FIG. 5, survival for individuals with low tumor mutational burden (<1.9 total mutations/Mb) was significantly better than individuals with high tumor mutational burden (≥1.9 total mutations/Mb). For those with low tumor mutational burden, median OS was 17.1 months (95% CI: 8.0, ∞), whereas median OS was 8.2 months (95% CI 4.9, 17.3) for those with high tumor mutational burden (Log-rank p=0.018). Cox model analysis was also conducted to assess the impact of total mutational burden on survival. The hazard ratio for individuals with high total variants (≥1.9) was 3.80 (95% CI: 1.17, 12.34; p=0.026). The Cox analysis indicates that as total tumor mutational burden increases, individual survival decreases (i.e., hazard increases).

TABLE 4

| | | Only samples prior to PVSRIPO: Overall survival by total variants (N = 31; 1 sample/individual *) | | | | |
|---|---|---|---|---|---|---|
| Group | Total | Median survival in months (95% CI) | 12-month survival (95% CI) | 24-month survival (95% CI) | 48-month survival (95% CI) | 60-month survival (95% CI) |
| Low (<1.9) | 16 | 16.5 (10.4, ∞) | 75% (46.3%, 89.8%) | 26.7% (6.9%, 52.2%) | 26.7% (6.9%, 52.2%) | 26.7% (6.9%, 52.2%) |
| High (≥1.9) | 15 | 9.4 (6.3, 14.3) | 46.7% (21.2%, 68.7%) | 7.8% (0.5%, 29.3%) | 0% | 0% |

Log-rank p = 0.018

*Note:

Using sample from immediately prior to PVSRIPO if available; otherwise using sample before and closest to PVSRIPO administration.

TABLE 4

Only samples immediately prior to PVSRIPO: Overall survival by total variants (N = 18)

| Group | Total | Median survival in months (95% CI) | 12-month survival (95% CI) | 24-month survival (95% CI) | 48-month survival (95% CI) | 60-month survival (95% CI) |
|---|---|---|---|---|---|---|
| Low (<1.9) | 10 | 17.1 (8, ∞) | 80% (40.9%, 94.6%) | 43.8% (11.9%, 72.6%) | 43.8% (11.9%, 72.6%) | 43.8% (11.9%, 72.6%) |
| High (≥1.9) | 8 | 8.2 (4.9, 17.3) | 37.5% (8.7%, 67.4%) | 0% | 0% | 0% |

Log-rank p = 0.018

In striking contrast to studies of tumor mutational burden and response to studies of tumor mutational burden and response to checkpoint inhibitors, a lower mutational burden was associated with a therapeutic effect and clinical benefit after treatment with PVSRIPO, as compared to a high mutational burden.

From samples obtained from a cohort of individuals treated in the study described in Example 1, whole-exome sequencing was performed, and sixty-six genes were analyzed for somatic mutations. From this analysis, identified were 82 mutational variants in 42 genes across samples from 7 individuals who did not show clinical benefit from immunotherapy comprising PVSRIPO administration (see, FIG. 6). These mutations appeared frequently in individuals that failed to respond to treatment with PVSRIPO. As evident from FIG. 6, the vast majority (greater or equal to 90%) of these mutations in these genes are C>T/G>A transitions (C to T mutations, G to A mutations). Further, analysis of samples from 2 of the 7 individuals demonstrated that mutations in these tumors comprise a hypermutated phenotype associated with treatment by an alkylating agent, wherein greater than 80% of the mutations are single base pair mutations that are C>T/G>A transitions (C to T mutations, G to A mutations). These 2 individuals were treated with the alkylating agent temozolomide prior to receiving immunotherapy with PVSRIPO, and failed to respond to treatment with PVSRIPO.

Example 3

Proxies for TMB

We have tested glioblastoma tumor samples for expression levels of genes related to enhanced immune responses such as TCR signaling pathway and cytolytic responses based on sequencing of RNA. We found that glioblastomas with low TMB trended with higher TCR signaling KEGG pathway enrichment compared to high TMB GBMs. When we compared Granzyme A and Perforin 1 transcripts we found that those glioblastomas with low TMB have higher cytolytic gene expression than those with high TMB. The cytolytic scores were inversely correlated with TMB. Additionally, the cytolytic scores correlated with enhanced immune responses such as TCR signaling pathway transcript enrichment.

Our data were obtained using recurrent glioblastomas that had undergone treatment with temozolomide. This treatment may actually cause the biological expression patterns that we observed. We did not observe the same associations in cohorts of newly diagnosed glioblastoma patients.

The invention claimed is:

1. A method of treating an individual having a tumor, comprising:
   (a) testing a tumor sample from the individual and determining its tumor mutational burden; and
   (b) upon determining a low mutational burden in the tumor sample, administering to the individual an immunotherapeutic agent comprising PVSRIPO.

2. The method of claim 1 wherein the immunotherapeutic agent comprising PVSRIPO comprises a combination of PVSRIPO and another immunotherapeutic agent other than PVSRIPO.

3. The method of claim 2 wherein the immunotherapeutic agent other than PVSRIPO is an immune checkpoint inhibitor.

4. The method of claim 2 wherein the immunotherapeutic agent other than PVSRIPO is an inducer of innate immunity.

5. The method of claim 2 wherein the immunotherapeutic agent other than PVSRIPO is an oncolytic virus.

6. The method of claim 1 further comprising administering to the individual a chemotherapeutic agent.

7. The method of claim 1 wherein the individual has been treated with an alkylating agent.

8. The method of claim 1 wherein the individual has a newly diagnosed tumor and the immunotherapeutic agent comprising PVSRIPO is administered prior to treatment with an alkylating agent.

9. The method of claim 1 wherein the tumor is a glioblastoma and a high tumor mutation burden is greater than or equal to 1.5 variants per Mb and a low tumor mutation burden is less than to 1.5 variants per Mb.

10. The method of claim 1 wherein the tumor is a melanoma and a high tumor mutation burden is greater than or equal to 20 variants per Mb and a low tumor mutation burden is less than to 20 variants per Mb.

11. The method of claim 1 wherein the tumor is a colorectal cancer and a high tumor mutation burden is greater than or equal to 17 variants per Mb and a low tumor mutation burden is less than to 17 variants per Mb.

12. A method of treating a population of at least a first and a second individual, each individual having a tumor, comprising:

testing a first tumor sample from the first individual and a second tumor sample from the second individual and determining tumor mutational burden in the first and second tumor sample, wherein (a) upon determining a high mutational burden in the first tumor sample, administering to the first individual a therapy that does not comprise PVSRIPO; and (b) upon determining a low mutational burden in the second tumor sample, administering to the second individual an immunotherapeutic agent comprising PVSRIPO.

13. The method of claim 12 wherein the therapy that does not comprise PVSRIPO is an immune checkpoint inhibitor.

14. The method of claim 12 wherein the therapy that does not comprise PVSRIPO is an inducer of innate immunity.

15. The method of claim 12 wherein the therapy that does not comprise PVSRIPO is an oncolytic virus.

* * * * *